United States Patent [19]

Schmidt et al.

[11] Patent Number: 5,002,680
[45] Date of Patent: Mar. 26, 1991

[54] MILD SKIN CLEANSING AEROSOL MOUSSE WITH SKIN FEEL AND MOISTURIZATION BENEFITS

[75] Inventors: Robert R. Schmidt, Ft. Wright, Ky.; Raymond H. Fortna; Harold H. Beyer, both of Cincinnati, Ohio

[73] Assignee: The Procter & Gamble Company, Cincinnati, Ohio

[21] Appl. No.: 379,702

[22] Filed: Jul. 12, 1989

Related U.S. Application Data

[63] Continuation of Ser. No. 223,743, Jul. 22, 1988, abandoned, which is a continuation of Ser. No. 23,940, Mar. 11, 1987, abandoned, which is a continuation of Ser. No. 707,308, Mar. 1, 1985, abandoned.

[51] Int. Cl.$^5$ .................. A61K 7/50; C11D 1/02; C11D 3/37; C11D 3/46
[52] U.S. Cl. .................. 252/90; 252/132; 252/546; 252/547; 252/554; 252/DIG. 5; 252/DIG. 14
[58] Field of Search ............ 252/90, 132, 546, 547, 252/554, DIG. 5, DIG. 14

[56] References Cited

U.S. PATENT DOCUMENTS

| | | | |
|---|---|---|---|
| 2,655,480 | 10/1953 | Spitzer | 252/90 |
| 2,979,465 | 4/1961 | Parran | 252/546 |
| 3,703,481 | 11/1972 | Barker | 252/546 |
| 3,819,524 | 6/1974 | Schubert | 252/90 |
| 3,852,417 | 12/1974 | McLaughlin | 424/47 |
| 3,923,970 | 12/1975 | Breuer | 424/73 |
| 3,959,160 | 5/1976 | Horsler et al. | 252/90 |
| 3,970,584 | 7/1976 | Hart | 252/305 |
| 4,140,648 | 2/1979 | Thompson | 252/90 |
| 4,292,212 | 9/1981 | Melby | 252/547 |
| 4,338,211 | 7/1982 | Stiros | 252/142 |
| 4,414,144 | 11/1983 | Liebowitz | 252/548 |
| 4,491,539 | 1/1985 | Hoskins et al. | 252/541 |
| 4,528,111 | 7/1985 | Su | 252/107 |

FOREIGN PATENT DOCUMENTS

| | | | |
|---|---|---|---|
| 858544 | 1/1961 | United Kingdom | 252/90 |
| 2103236A | 2/1983 | United Kingdom | |

OTHER PUBLICATIONS

Cosmetics & Toiletries, vol. 91, Jul. 1976, pp. 66–70.

Primary Examiner—Dennis Albrecht
Attorney, Agent, or Firm—Robert B. Aylor; Richard C. Witte

[57] ABSTRACT

A mild skin-cleansing aerosol mousse-forming emulsion providing benefits in leaving the skin after washing feeling not taut and dry, but moisturized, soft and smooth. The product also provides abundant rich creamy foam. The cleansing mousse emulsion comprises:

A. 88% to 97% of a concentrate containing by weight of the concentrate:
  1. from 3% to 20% of a mild nonsoap anionic or amphoteric surfactant;
  2. a polymeric skin feel aid at 0.05% to 5%;
  3. a moisturizer at 10% to 60%, preferably glycerin;
  4. the balance water; and
B. from 3% to 12% of a propellant by weight of the total emulsion.

19 Claims, No Drawings

MILD SKIN CLEANSING AEROSOL MOUSSE WITH SKIN FEEL AND MOISTURIZATION BENEFITS

This is a continuation of application Ser. No. 07/223,743, filed Jul. 22, 1988 now abandoned, which is a continuation of application Ser. No. 07/023,940, filed on Mar. 11, 1987, now abandoned, which is a continuation of application Ser. No. 06/707,308, filed on Mar. 1, 1985, now abandoned.

TECHNICAL FIELD

The present invention is related to mild personal skin cleansers. More particularly, this invention relates to pressurized aerosol mousse dispensers of skin cleansers comprising surfactants and other cleansing aids.

BACKGROUND OF THE INVENTION

In pressurized foam dispensers of the above-mentioned type, a foamable concentrate, generally an aqueous soap solution, is contained in a dispenser equipped with a dispensing head and valve, and pressurized with a normally gaseous propellant, e.g., a low molecular weight hydrocarbon or hydrocarbon mixture or a halohydrocarbon or halohydrocarbon mixture. Upon discharge of the emulsion through the dispensing head the volatilization of the dispersed liquid droplets of propellant causes the dispensed concentrate to foam. Depending upon the precise formulation of the concentrate, the dispensed product may range from a dense creamy foam to a light foam.

The term "emulsion" will be used throughout this specification and claims to refer to the whole liquid contents of the dispenser, i.e., the foamable concentrate plus liquid phase propellant, and the term "concentrate" will be used to refer to the liquid contents of the dispenser, other than the propellant, "liquid" in this context embracing solutions, emulsions and suspensions. In other words, the concentrate itself may be an emulsion or suspension and not necessarily a solution of the foam producing ingredients in a suitable liquid medium, which, in the case of the present invention, will be water. The term "mousse", as used herein, is the same as foam, and refers to the dispensed product unless otherwise specified.

The cleaning of skin with surface-active cleaning preparations has become a focus of great interest. Many people wash and scrub their skin with various surface-active preparations several times a day. Ideal skin cleansers should cleanse the skin gently, causing little or no irritation without defatting and overdrying the skin or leaving it taut after frequent routine use. Most lathering soaps, liquids and bars included, fail in this respect.

Certain synthetic surfactants are particularly mild. However, a major drawback of most mild synthetic surfactant systems when formulated for skin cleansing is poor lather performance compared to the highest bar soap standards (bars which are rich in coconut soap and superfatted). On the other side, the use of known high sudsing anionic surfactants with lather boosters can yield acceptable lather volume. Unfortunately, however, the highest sudsing anionic surfactants are, in fact, poor in clinical skin mildness. Surfactants that are among the mildest, such as sodium lauryl glyceryl ether sulfonate, (AGS), are marginal in lather. These two facts make the surfactant selection, the lather and skin feel benefit formulation process a delicate balancing act.

Moisturizers provide skin conditioning benefits. E.g., it is known that glycerin is added to bars and liquid cleansing products for skin benefits. Glycerin in liquids at levels of greater than 8% is extremely difficult to lather and in nonsoap bars is difficult to process. Glycerin has also been used in a soap based shaving cream at a 10% level.

U.S. Pat. No. 3,959,160, Horsler et al., issued May 25, 1976, discloses aerosol shaving foam compositions which comprise soaps or nonsoap anionic surfactants and fatty alcohols. The Horsler et al. examples include up to 5% glycerin. This patent does not disclose higher levels of moisturizer or polymeric skin feel aids.

Examples of mild liquid cleansing compositions are disclosed in the following references. U.S. Pat. No. 4,338,211, Stiros, issued Jul. 6, 1982, discloses liquid skin cleanser with 2.3% to 3% AGS, the polymer JR400 and small amounts of free fatty acid plus a fatty acid alkylolamide as lather boosting agents. Compositions containing the surfactants AGS, betaine and sarcosinate are not disclosed.

U.S. Pat. No. 4,491,539, James J. Hoskins and Adriaan Kessler, issued Jan. 1, 1985, discloses liquid cleansing products comprising about 5% to 30% of surfactant, about 0.1% to about 1.0% of guar material, about 0.15% to about 1.0% of nonionic carboxyvinyl polymer, and water. Exemplary compositions containing the surfactants AGS, betaine and sarcosinate are not disclosed. British Pat. No. 2,103,236A, Colgate, Feb. 16, 1983, discloses a light duty, liquid detergent containing guar gum, a ternary surfactant mixture including betaine. AGS is not used. British Pat. No. 2,114,994A, L'Oreal, Sept. 1, 1983, discloses a cleansing product based on acylisethionates and cationic polymers, and is incorporated herein by reference.

Rather stringent requirements for skin cleansers limit the choice of surface-active agents, and final formulations represent some degree of compromise. Mildness is often obtained at the expense of effective cleansing, or lathering may be sacrificed for either mildness, product stability, or both.

None of the above-cited prior art formulations contain the composition of mild synthetic surfactant, high level of moisturizer with polymer skin feel aids.

OBJECTS OF THE INVENTION

Therefore, one object of this invention is the development of skin cleaning compositions which exhibit desired skin feel after washing together with effective cleansing through surface activity and abundant rich, creamy foam. The desired skin feel is achieved through the combined action of mild surfactants, skin feel polymer and high levels of moisturizers which act together to leave the skin feeling less taut/dry, more moisturized, softer and smoother after washing.

Other objects will become apparent from the detailed description below.

SUMMARY OF THE INVENTION

The present invention offers a valuable combination of desirable properties to skin cleaning formulations. The invention provides a mild skin cleansing mousse having a superior combination of rich, creamy foam and skin feel after washing leaving the skin feeling less taut/dry, more moisturezed, softer and smoother. The cleansing mousse product comprises a pressurized dispenser equipped with a dispensing head and valve, the dispenser containing therein a foam-forming emulsion.

The cleansing emulsion comprises: 88% to 97% of a concentrate and 3-12% of a propellant. The concentrate comprises:
1. from 3% to 20% of a mild nonsoap surfactant selected from anionic and amphoteric surfactants;
2. a polymeric skin feel aid at 0.05% to 5%;
3. a moisturizer at a level of 10% to 60%; and
4. the balance water.

The concentrate of the present invention contains from about 15% to about 87% water, preferably from about 35% to about 75% water.

DETAILED DESCRIPTION OF THE INVENTION

The invention relates to a skin cleaning mousse with superior after washing skin feel combined with rich, creamy foam. This mild cleansing mousse composition is believed to provide less skin irritation and facial tautness than commercially available toilet soap bars, synthetic toilet bars or other known specially lathering facial cleansing products. The mousse of this invention also provides abundant, rich creamy foam and leaves the skin feeling soft and smooth after washing.

The preferred mousse concentrate contains: 15-40% glycerin; 6-12% alkyl glyceryl ether sulfonate (AGS) plus a co-surfactant selected from (i) anionic alkyoyl (acyl) sarcosinate or (ii) amphoteric betaine or sultaine, or mixtures thereof; and 0.1-1% polymeric skin feel aid selected from cationic polymers including guar gums, cellulosic resins; homopolymers and copolymers of dimethyldiallylammonium chloride and nonionic guar gums.

Moisturizers/Emollients

Moisturizers are included to provide the skin conditioning benefits and to aid in leaving the skin feeling less taut/dry, more moisturized, softer and smoother after washing. The aerosol product form surprisingly allows very high levels of the moisturizers to be incorporated without adversely affecting the foamforming ability of the product or its in-use feel, thereby delivering better after washing skin feel than heretofore available from conventional lathering liquid cleansers.

The moisturizers useful in the present invention are used at a level of 10% to 60% by weight of the concentrate. The preferred levels of moisturizers are, respectively, 12% to 40% and 15% to 40%. The preferred moisturizers are the nonocclusive liquid water-soluble polyols and the essential amino acid compounds found naturally in the skin. The most preferred moisturizer is glycerin. The moisturizer, at these levels, provides superior after washing skin feel, less taut, more moisturized, softer and smoother. The mousse of the present invention is surprisingly stable. In the mousse formulation of this invention the high level of moisturizer can also provide an enhanced creamy foam.

The term "moisturizer" is often used within the cosmetic industry without very exact definition. The term is sometimes used as synonymous with emollient, and is then meant to describe a material which imparts a smooth and soft feeling to the skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect.

Both occlusive and nonocclusive moisturizers work in the present invention. The preferred is the nonocclusive moisturizer. Some examples of the more preferred nonocclusives are liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

Other preferred nonocclusive moisturizers are the compounds which are found to be naturally occurring in the stratum corneum of the skin, such as sodium pyrrolidone carboxylic acid, lactic acid, urea, L-proline, guanidine and pyrrolidone. Examples of other water-soluble nonocclusive moisturizers include water-soluble hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), hydrolyzed protein and other collagen-derived proteins, aloe vera gel and acetamide MEA.

The occlusive type moisturizers include petrolatum, mineral oil, beeswax, silicone oil, lanolin and oil-soluble lanolin derivatives, saturated and unsaturated fatty alcohols such as behenyl alcohol, hydrocarbons such as squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizers are disclosed in "Emollients—A Critical Evaluation," by J. Mausner, Cosmetics & Toiletries, May 1981, incorporated herein by reference. Free fatty acids are also acceptable moisturizers.

The Surfactant

Preferred mild anionic and amphoteric surfactants used in this invention include: alkyl glyceryl ether sulfonate (AGS), anionic acyl sarcosinates, methyl acyl taurates, N-acyl glutamates, acyl isethionates, alkyl sulfosuccinate, alkyl phosphate ester, ethoxylated alkyl phosphate esters, trideceth sulfate, protein condensates, mixtures of ethoxylated alkyl sulfates and alkyl amine oxides, betaines, sultaines, and mixtures thereof. Alkyl chains for these surfactants are $C_8$-$C_{22}$, preferably $C_{10}$-$C_{18}$.

A preferred primary mild surfactant is sodium coco glyceryl ether sulfonate, which is mild and relatively nonirritating to the skin. This has been demonstrated in in vitro testing. While desirable to incorporate into a facial cleanser for its mildness properties, this coco AGS alone does not provide sufficient lather volume or speed of lather and produces a large, open bubble lather not of the rich, creamy small bubbled type desirable in facial cleansing. A 90/10 coconut/tallow alkyl distribution is most preferred. Certain secondary co-surfactants used in combination with AGS can provide a creamier and more stable foam. These secondary surfactants must also be intrinsically mild. Two secondary surfactants have been found to be especially desirable: a zwitterionic surfactant of the betaine class 70/30 laur/myristamidopropyl betaine (trade name Lexaine LM, made by Inolex Corp.), and an anionic, sodium lauroyl sarcosinate (trade name Hamposyl L, made by Hampshire Chemical).

Nonionics cannot be used as the sole surfactant in this product because of their low foaming ability; however, they can be incorporated as a co-surfactant. Examples of preferred nonionic surfactants are alkyl glucosid and methyl glucose esters. The amphoteric betaines and sultaines can be used as the sole surfactant, but are more preferred as a co-surfactant. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfo betaines may be represented by coco sultaine, stearyl sultaine, lauryl dimethyl ethyl sulfobetaine, lauryl bis(2-hydroxyethyl propyl sulfobetaine and the like; amido betaines and amidosulfobetaines, wherein the $RCONH(CH_2)_3$ radical is attached to the nitrogen atom and are also useful in this invention.

It was also learned that the betaine employed in compositions of this invention (Lexaine LM) can provide an additional benefit of soft/smooth skin feel through a desquamation effect, i.e., removal of dead skin cells (dry skin flakes) in in vitro testing. Although the zwitterionic surfactants of the betaine class (cetyl betaines like Lonzaine 16S) are known to have this capability, generally it has been thought that the alkyl group chain length should be $C_{16}$ or higher. It was a surprising finding that the low levels of $C_{12}$–$C_{14}$ alkyl betaine employed in this development would provide a factor of 2× improvement in scale (i.e., dry skin flakes) removal vs. other facial cleansing products or a similar formulation not including the preferred betaine.

Therefore, a tri-component surfactant system of three surfactants employed in this invention (AGS, Lexaine LM, sodium lauroyl sarcosinate) is highly desirable for the mousse of the present invention.

The ratios of AGS to co-surfactant are variable from 1:1 to 5:1, preferably 2:1 to 4:1. Also, three component mixtures of AGS/Lexaine LM/sarcosinate are believed desirable.

Other amphoterics of the betaine class are usable, i.e., cocamidopropyl betaine, cetyl betaine or sultaines.

Mixtures of ethoxylated alkyl sulfate and alkyl amine oxides have been found within certain ratios to provide mild surfactancy. A mole fraction of 0.5–1.0 amine oxide to alkyl sulfate is particularly mild as reported by K. Miyazawa et al., in *The International Journal of Cosmetic Science*, Vol. 6, (1984), pp. 33–46.

Other chain lengths ($C_{10}$–$C_{18}$) of any of the above mild surfactants or co-surfactants such as sodium myristoyl sarcosinate, etc., are also usable in this invention. Salts other than the sodium salt such as K-AGS and chain length distributions other than 90/10 coconut/tallow are usable.

The Polymeric Skin Feel Aids

The polymeric skin feel aids useful in the present invention are the cationic and the nonionic polymers used in the cosmetic field. Reduced skin irritation benefits of both types of polymers are set out in "Polymer JR for Skin Care" Bulletin, by Union Carbide, 1977. The cationics are preferred over the nonionic because they provide better skin feel benefits. Examples of the cationic polymers and the nonionic polymers useful in the present invention are set out below.

The amount of polymeric skin feel aid found useful in the concentrate is from about 0.05% to about 5%, preferably from about 0.1% to about 2%, and more preferably 0.1% to 1.0%.

In order to achieve superior after washing skin feel for this mousse, i.e., leaving the skin feeling less taut/more moisturized, softer and smoother, it was discovered that a combination of a high level of moisturizer (10–60% in the concentrate) and a selected polymeric ingredient, e.g., cationic (quaternized) guar gum (e.g., Jaguar C-14-S), is required.

Other types of high molecular weight polymeric skin feel agents, such as nonionic guar gums, Merquats 100 and 550, made by Merck & Co., Inc; UCARE Polymer JR-400, made by Union Carbide Corp.; Mirapol A15 made by Miranol Chemical Company, Inc.; and Galactasol 811, made by Henkel, Inc.; plus others, are usable. The polymer also provides enhanced creamy foam benefits.

The nonionic polymers found to be useful include the nonionic polysaccharides, e.g., nonionic hydroxypropyl guar gums, offered by Celanese Water Soluble Polymers, a Division of Celanese Corp. A preferred nonionic hydroxypropyl guar gum material is Jaguar® HP-60 having molar substitution of about 0.6. Another class of useful nonionics is the cellulosic nonionic polymers, e.g., HEC and CMC.

The cationic polymers employed in this invention also provide a desirable silky, soft, smooth in-use feeling. The preferred level for this invention is 0.1–1% of the concentrate. While not being bound to any theory, it is believed that cationic polymers chemically interact with the anionic surfactants (e.g., AGS and sarcosinates) to form complexes which may enhance the mildness to skin characteristics of the already mild surfactants. Also, there is reason to believe that the positively charged cationic polymers can bond with negatively charged sites on the skin to provide a soft skin feel after use. Not to be bound by any theory, it is believed that the greater the charge density of the cationic polymer, the more effective it is for skin feel benefits.

One preferred cationic polymer is a cationically substituted galactomannan gum. The gum occurs naturally as guar gum, the principal component of the seed of the guar plant, *cyamopsis tetragonalobus*. The guar molecule is essentially a straight chain mannan branched at quite regular intervals with single membered galactose units on alternative mannose units. The mannose units are linked to each other by means of beta (1–4) glycosidic linkages. The galactose branching is accomplished through an alpha (1–6) linkage. The cationic derivatives are obtained by reaction between the hydroxyl groups of the polygalactomannan and reactive quaternary ammonium compounds. The degree of substitution "n" of the cationic groups is 0.11 to 0.22. The general formula for this cationic polymer is:

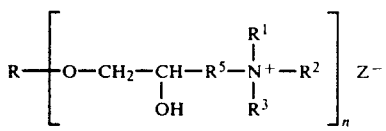

where R represents guar gum.

An example of a suitable quaternary ammonium derivative is hydroxypropyltrimethylammonium guar gum of the formula:

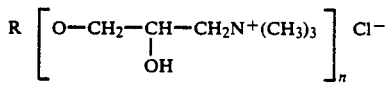

Such a material is available commercially from Celanese Water Soluble Polymers, a Division of Celanese Corp., Clifton, N.J. 07012, under the trade name JAGUAR® C-14-S. This material also has the CTFA designation Guar Hydroxypropyltrimonium Chloride. Another suitable material is that known as JAGUAR C-17 which is similar to JAGUAR C-14-S, but has a higher degree of substitution of cationic groups. A further example of a suitable guar derivative is the hydroxypropylated cationic guar derivative known as JAGUAR C-16 which, as well as containing the above cationic quaternary ammonium groups, also contains hydroxypropyl ($-CH_2CH(OH)CH_3$) substituent groups. JAGUAR C-16 has a degree of substitution of the hydroxypropyl groups being 0.8–1.1.

Other suitable cationic polymers are copolymers of dimethylaminoethylmethacrylate and acrylamide and copolymers of dimethyldiallylammonium chloride and acrylamide in which the ratio of the cationic to neutral monomer units has been selected give a copolymer having a cationic charge.

A more complete list of cationic polymers useful in the present invention is described in U.S. Pat. No. 4,438,095, to Grollier/Allec, issued Mar. 20, 1984, incorporated herein by reference. Some of the more preferred cationics are listed in Col. 3, section 2; Col. 5, section 8; Col. 8, section 10; and Col. 9, lines 10–15 of the Grollier/Allec patent, incorporated herein by reference.

The Propellant

The propellants used in the compositions of the present invention are conventional materials, e.g., hydrocarbon and hydrocarbon mixtures, e.g., the mixture of butane, isobutane and propane, known commercially as Propellant A46, made by Phillips Chemical Co., a subsidiary of Phillips Petroleum Company, ethers and halohydrocarbons such as dimethyl ether or dichlorodifluoromethane (12) alone or mixtures thereof with dichlorotetrafluoroethane (114). Mixtures of hydrocarbon and halohydrocarbon propellants and nitrous oxide may also be used. The quantity of propellant used will generally be in the range of 3–12% by weight of the total emulsion. Preferred is 4–10% propellant.

Other Ingredients

It is preferred that the cleansing product be formulated to provide a pH in use within the range of from about 5 to about 6, depending upon the particular surfactant or materials employed. Any of a large number of known substances can be used to adjust the pH of the liquid cleansing product, e.g., sodium hydroxide to raise the pH, citric acid to lower the pH, generally at a level of up to about 0.5% of the concentrate.

Emulsifiers may be added to the formula to improve the phase stability of the concentrate; however, they are not necessary for a stable aerosol product that would be shaken before use—any slight phase separation is readily mixed into a homogeneous solution with only slight agitation.

Emulsifiers either alone or in combination with other formula ingredients, should be mild so as not to adversely affect the mildness of the total formula. Soaps, which are good emulsifiers, are acceptable at a level of 0.1–5% of the concentrate. An emulsifier such as PEG-600 is useful in the present invention at a level of 2–6% of the concentrate.

Other emulsifiers can be selected from the group consisting of polyethoxylated $C_8$–$C_{22}$ fatty acids having less than about 30 moles of ethylene oxide per mole of fatty acid, ethoxylated esters, unethoxylated sugar esters, polyoxyethylene fatty ether phosphates, fatty acid amides, phospholipids, polypropoxylated fatty ethers, acyl lactylates, polyethoxylated poly (oxypropylene) glycols, polypropoxylated poly (oxyethylene) glycols, poly (oxyethylene) poly(oxypropylene) ethylene diamines, and mixtures thereof.

Examples of such emulsifiers include polyoxyethylene (8) stearate, myristyl ethoxy (3) palmitate, methyl glucoside sesquistearate, sucrose distearate, sucrose laurate, sorbitan monolaurate, polyoxyethylene (3) oleyl ether phosphate, polyoxyethylene (10) oleyl ether phosphate, lauric diethanolamide, stearic monoethanolamide, lecithin, lanolin alcohol propoxylates, sodium stearoyl-2-lactylate, calcium stearoyl-2-lactylate and the Pluronics offered by BASF Wyandotte.

Preferred emulsifiers are the polyethoxylated fatty acids having less than about 30 moles of ethylene oxide per mole of fatty acid, ethoxylated esters and the acyl lactylates.

It is also desirable to include a rinse aid in this product such as long chain length fatty acids (stearic acid), various clays, dry flow starch, Zn/Mg/Al stearate, calcium carbonate, precipitated amorphous silica, an amphoteric betaine or sultaine, or a selected nonionic surfactant. The preferred rinse aids are nonionic surfactants and fatty acids and mixtures thereof. The preferred nonionic surfactant rinse aid is a water-soluble polyoxyethylene derivative of a hydrophobic base, said derivative being a member of the group consisting of:

a. The reaction products of 9–20 carbon atom fatty acid monoesters of aliphatic polyhydric alcohols, which polyhydric alcohols contain at least 3 hydroxyls, with at least 10 moles of ethylene oxide;

b. The reaction products of 9–20 carbon atom alcohols, acids and mercaptans with at least two-thirds as many ethylene oxide units as the number of carbon atoms in the hydrophobic base, such as $AE_{12}$ and $C_{10}E_{10}$ ethoxylated anionics;

c. The reaction products of 12–24 carbon atoms alkylphenols and alkylcyclohexanols with at least as many ethylene oxide units as the number of carbon atoms in the hydrophobic base; and d. Block copolymers of propylene oxide and ethylene oxide having the formula:

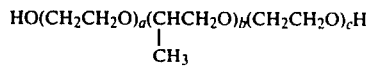

wherein a is an integer greater than seven, b is an integer from about five to about 20, and c is an integer, all such that (a plus c) is at least equal to b and is preferably at least twice b. This latter condition on the structure of useful block copolymers is designed to include only those which are sufficiently hydrophilic to give adequate stable foam. The useful block copolymers should also have a molecular weight from about 1,000 to about 20,000.

A preferred nonionic surfactant is polysorbate-20 (Tween 20 made by ICI Americas, Inc.) which can be used in the mousse product of the present invention at a level of 1–10%, more preferably 3–8% of the concentrate.

Long chain saturated and unsaturated fatty acids, preferably stearic acid, can be used as a rinse aid in the mousse products of the present invention at a level of 0.25% to 10%, preferably 0.5% to 5% of the concentrate.

Fatty alcohols, $C_{10}$–$C_{18}$, preferably myristyl alcohol at a level of 0.05% to 5% of the concentrate, more preferably at about 0.1% can be used in the present invention.

Perfumes may be used in the cleansing products, generally at a level of about 0.1% to about 1% of the concentrate. Colorants may also be used. Opacifiers, e.g., ethylene glycol distearate, polystyrene latex, generally at a level of about 0.2% of the concentrate, may also be used to provide the mousse with an opaque or pearlescent appearance. Preservatives, e.g., EDTA, methyl paraben, propyl paraben, Germall 115, Kathon, generally at a level of less than 1% of the concentrate, may be incorporated in the emulsion to prevent microbiological growth.

Split Face Wash Panel Test (In Vivo)

This test is conducted using expert female panelists who are sensitive to facial skin effect differences. The products were alternated between left and right sides of the face, as well as by order of the panelists.

The key question asked was "Which side of your face feels tighter?" Facial tautness is a key indicator of perceived mildness and the moisturization ability of a skin cleansing product.

The Method

Mousse - Mousse Test

1. Wet hands and face with water.
2. Shake can well before using.
3. Dispense a one inch puff (20–25 ml = 0.8–1.25 g) nominally 1 g of mousse onto fingers or a wet wash cloth (do the same way as other product).
4. Apply the product to the appropriate side of face and rub gently, being careful not to get any product on the other half of face.
5. Rinse face with water, but do not dry.

Now, pat dry both sides of face with a paper towel. Wait 10 minutes, then answer the question "Which side of your face feels tighter?"

Bar - Mousse Test

Same as Mousse - Mousse Test except one side of face is washed using the bar soap in usual manner (water only or with wash cloth).

|    | Parts | EXAMPLES A-E | | | | |
|----|-------|---|---|---|---|---|
|    |       | A | B | C | D | E |
| 94 | concentrate | % | % | % | % | % |
|    | AGS | 6 | 6 | 6 | 6 | 6 |
|    | Hamposyl L* | 2 | 2 | 2 | 2 | 2 |
|    | Lauryl Alcohol | 0.2 | 0.2 | 0.2 | — | — |
|    | Glycerin | 15 | 20 | 5 | 15 | 5 |
|    | Jaguar C-14-S | 0.25 | 0.25 | — | 0.25 | — |
|    | Stearic Acid | 1 | 0.25 | 1 | — | — |
|    | Tween 20* | — | 4 | — | — | — |
|    | Hydrolyzed Protein | 0.45 | 0.45 | 0.45 | — | — |
|    | Aloe Vera Gel | 1 | 1 | 1 | — | — |
|    | PEG-600 | 4 | 4 | 4 | — | — |
|    | Perfume | 0.2 | 0.2 | 0.2 | 0.2 | 0.2 |
|    | Minors | 0.7 | 0.7 | 0.7 | 0.7 | 0.7 |
|    | Water | Balance | Balance | Balance | Balance | Balance |
|    |       | (Balance to 100 Parts concentrate) | | | | |
|    | pH | 5-6 | 5-6 | 5-6 | 5-6 | 5-6 |
| 6  | Propellant A-46 | 6 | 6 | 6 | 6 | 6 |
| 100 | Parts | | | | | |

*Defined hereinabove.

TABLE 1
Split Face Wash Panel Test Results

| Examples A vs. C | | |
|---|---|---|
| Less facial tautness | 84/14 | statistically significant at a 99% confidence level |
| More smooth after-feel | 74/26 | statistically significant at a 90% confidence level |
| Examples D vs. E | | |
| Less facial tautness | 64/36 | statistically significant at a 95% confidence level |
| More smooth after-feel | 59/41 | statistically significant at a 80% confidence level |

The above test results show that Example A of the present invention, with 15% glycerin and 0.25% polymer, is significantly milder than Example C, which has only 5% glycerin and no polymers, at confidence levels of 99% and 90%. Examples D vs. E compares the same base formulas as Examples A vs. C with the nonessential ingredients omitted.

| Example A vs. DOVE ® Bar* | | |
|---|---|---|
| Less facial tautness | 67/33 | statistically significant at a 98% confidence level |
| Less redness | 59/41 | statistically significant at an 80% confidence level |

The test of mousse Example A vs. DOVE bar soap shows an advantage for the mousse product in terms of mildness and less irritation as measured by facial tautness and red appearance of the face after washing. The DOVE bar is an accepted marketplace mildness benchmark.

*The formula for DOVE ® is estimated to be:

TABLE 2

| Na Soap (T/Cn) | 11.7 | (85/15) |
|---|---|---|
| Na Cocoyl Isethionate | 44.0 | |
| Stearic Acid | 26.0 | |
| Water | 7.0 | |
| Cn Fatty Acid | 2.5 | |
| NaCl | 0.35 | |
| Perfume | 1.25 | |
| NaLAS | 1.80 | |
| Na Isethionate | 2.60 | |
| Na Stearate | 2.40 | |
| TiO$_2$ | 0.40 | |
| Total | 100.00 | |

These data show that the mousse of this invention results in the desired mild skin cleansing action with improved skin feel leaving the skin feeling less taut and dry and more moisturized, softer and smoother.

Additional High Moisturizer Level Example

| Parts | | |
|---|---|---|
| 94 | concentrate | % |
| | AGS | 6 |
| | Lamposyl L* | 2 |
| | Lauryl Alcohol | 0.2 |
| | Mineral Oil | 40 |
| | Jaguar C-14-S | 0.25 |
| | Stearic Acid | 1 |
| | Hydrolyzed Protein | 0.45 |
| | Aloe Vera gel | 1 |
| | PEG-600 | 4 |
| | Perfume | 0.2 |
| | Minors | 0.8 |
| | Water | Balance |
| | | (To 100 parts concentrate) |
| | pH | 5–6 |
| 6 | propellant A-46 | 6 |
| 100 | Parts | |

*Defined Hereinabove.

This is an example of a product having a 40% moisturizer level in the concentrate. It exhibits excellent moisturization, skin feel leaving the skin less taut, less dry, more moisturized. It also has excellent foam properties.

What is claimed is:

1. A skin-cleansing emulsion mousse-forming product having a pressurized dispenser equipped with a dispensing head and valve and containing therein a foam-forming emulsion consisting essentially of;
    A. 88% to 97% of a concentrate containing by weight of the concentrate consisting essentially of:
        1. from 3% to 20% of a mild nonsoap surfactant selected from the group consisting of mild anionic and mild amphoteric surfactants selected from the group consisting of: alkyl glyceryl ether sulfonate (AGS); anionic acyl sarcosinates; methyl acyl taurates; N-acyl glutamates; acyl isethionates; alkyl sulfosuccinate; alkyl phosphate ester; ethoxylated alkyl phosphate esters; protein condensates; mixtures of ethoxylated alkyl sulfates and alkyl amine oxides; betaines; sultaines; and mixtures thereof;
        wherein the alkyl chains for said surfactants are from about $C_8$ to about $C_{22}$;
        2. a polymeric skin feel aid at 0.05% to 5% wherein said polymer is selected from the group consisting of cationic and nonionic polysaccharides; cationic and nonionic homopolymers and co-polymers derived from acrylic and/or methacrylic acid; cationic and nonionic cellulosic resins; cationic copolymers and dimethyldiallylammonium chloride and acrylic acid; cationic homopolymers of dimethyldiallylammonium chloride; cationic polyalkylene and ethoxypolyalkylene imines, and mixtures thereof;
        3. from 10% to 60% of a moisturizer selected from the group consisting of sodium pyrrolidone carboxylic acid, sodium lactate, hexadecyl, myristyl, isodecyl, or isopropyl esters of adipic, lactic, oleic, stearic, isostearic, myristic and linoleic acids, and their corresponding alcohol esters, sodium isostearoyl-2-lactylate and sodium capryl lactylate, glycerin, polyethylene glycol, propylene glycol, sorbitol, polyethylene glycol and propylene glycol ethers of methyl glucose, polyethylene glycol and propylene glycol ethers of lanolin alcohol, lactic acid, L-proline, other free fatty acids, and mixtures thereof; and wherein when said moisturizer is selected from the group consisting of only said glycerine, said sorbitol, said polyethylene glycol and mixtures thereof, said level of moisturizer is present at at least 12% of said concentrate;
        4. balance water; and
    B. from 3% to 12% of a propellant by weight of the total emulsion said cleansing product being formulated to provide a pH in use within the range of from about 5 to about 6.

2. The skin-cleansing emulsion mousse-forming product of claim 1 wherein the moisturizer is nonocclusive and is selected from the group of:
    1. water-soluble liquid polyols;
    2. essential amino acid compounds found naturally occurring in the stratum corneum of the skin;
    3. water-soluble nonpolyol nonocclusives and mixtures thereof.

3. The skin-cleansing emulsion mousse-forming product of claim 2 wherein said moisturizer is selected from the group consisting of said amino acid compounds and said liquid polyols.

4. The skin-cleansing emulsion mousse-forming product of claim 1 wherein said moisturizer is glycerin.

5. The skin-cleansing emulsion mousse-forming product of claim 1 wherein said moisturizer is present at a level of 12% to 40% of the concentrate.

6. The skin-cleansing emulsion mousse-forming product of claim 1 wherein said polymer is at 0.1% to 2%; and said glycerin is at 12% to 40% of the concentrate.

7. The skin-cleansing emulsion mousse-forming product of claim 1 wherein said mild surfactant is an alkyl glyceryl ether sulfonate/sarcosinate mix having a ratio of 1:1 to 5:1.

8. The skin-cleansing emulsion mousse-forming product of claim 7 wherein said alkyl glyceryl ether sulfonate/sarcosinate has a ratio of 2:1 to 4:1.

9. The skin-cleansing emulsion mousse-forming product of claim 1 wherein said concentrate also contains a co-surfactant selected from the group consisting of nonionic betaine or sultaine surfactants, and wherein the mild surfactant and the co-surfactant have a ratio of 1:1 to 5:1, and wherein said mild non-soap surfactant is other than betaine and sultaine.

10. The skin-cleansing emulsion mousse-forming product of claim 9 wherein said concentrate contains from 1% to 10% of a nonionic surfactant.

11. The skin-cleansing emulsion mousse-forming product of claim 9 wherein said nonionic is 3% to 8% of the concentrate.

12. The skin-cleansing emulsion mousse-forming product of claim 1 wherein said concentrate contains from 0.25% to 10% stearic acid.

13. The skin-cleansing emulsion mousse-forming product of claim 1 wherein said concentrate contains from 0.5% to 5% stearic acid.

14. The skin-cleansing emulsion mousse-forming product of claim 1 wherein said concentrate contains fatty alcohol at a level of 0.05% to 5%.

15. The skin-cleansing emulsion mousse-forming product of claim 1 wherein said concentrate contains fatty alcohol at a level of 0.05% to 1%.

16. The skin-cleansing emulsion mousse-forming product of claim 1 wherein said polymer is at 0.1% to 1%; said glycerin is at 15% to 40%; and said concentrate contains stearic acid at 0.5% to 5% and $C_{10}$–$C_{18}$ fatty alcohol at 0.1%.

17. The skin-cleansing emulsion mousse-forming product of claim 1 wherein said concentrate contains from 2% to 6% of polyethylene glycol having a molecular weight of about 600.

18. The skin-cleansing emulsion mousse-forming product of claim 1 wherein said concentrate also contains from 0.1% to 5% of a hydrolyzed protein.

19. The skin-cleansing emulsion mousse-forming product of claim 1 wherein said concentrate contains from 0.5% to 5% aloe vera gel.

* * * * *

UNITED STATES PATENT AND TRADEMARK OFFICE
CERTIFICATE OF CORRECTION

PATENT NO. : 5,002,680
DATED : March 26, 1991
INVENTOR(S) : Robert R. Schmidt, Raymond H. Fortna & Harold H. Beyer It is certified that error appears in the above-identified patent and that said Letters Patent is hereby corrected as shown below:

Col. 5, line 6, "glucosid" should read -- glucosides --.

Col. 6, line 68, after "gum." insert --
In the above formula, $R^5$ can be an alkylene group containing from one to three carbon atoms; $R^1$, $R^2$, and $R^3$ can be radicals containing not more than 18 carbon atoms; and Z is an anion, such materials being known in the art, as set forth, e.g., in U.S. Patent 3,589,978 which is referred to in U.S. Patent 4,438,095, infra. The degree of substitution set forth hereinbefore, determines the value of "n". --.

Col. 11, line 28 to Col. 12, line 12, delete Claim 1 and insert therefor --
1. A skin-cleansing emulsion mousse-forming product with excellent foam properties and skin conditioning benefits to leave the skin feeling less taut/dry, more moisturized, softer and smoother, said product having a pressurized dispenser equipped with a dispensing head and valve and containing therein a foam-forming emulsion consisting essentially of;
   A.   88% to 97% of a concentrate containing by weight of the concentrate consisting essentially of:

UNITED STATES PATENT AND TRADEMARK OFFICE
CERTIFICATE OF CORRECTION

PATENT NO. : 5,002,680
DATED : March 26, 1991
INVENTOR(S) : Robert R. Schmidt, Raymond H. Fortna & Harold H. Beyer It is certified that error appears in the above-identified patent and that said Letters Patent is hereby corrected as shown below:

1. from about 6% to about 12% of a mild nonsoap surfactant selected from the group consisting of mild anionic and mild amphoteric surfactants selected from the group consisting of:

alkyl glyceryl ether sulfonate;

anionic acyl sarcosinates;

methyl acyl taurates;

N-acyl glutamates;

acyl isethionates;

mixtures of ethoxylated alkyl sulfates and alkyl amine oxides;

betaines;

sultaines; and mixtures thereof;

wherein the alkyl chains for said surfactants are from about $C_8$ to about $C_{22}$;

2. a polymeric skin feel aid at 0.1% to 2% wherein said polymer has the general formula:

UNITED STATES PATENT AND TRADEMARK OFFICE
CERTIFICATE OF CORRECTION

PATENT NO. : 5,002,680

DATED : March 26, 1991

INVENTOR(S) : Robert R. Schmidt, Raymond H. Fortna & Harold H. Beyer

It is certified that error appears in the above-identified patent and that said Letters Patent is hereby corrected as shown below:

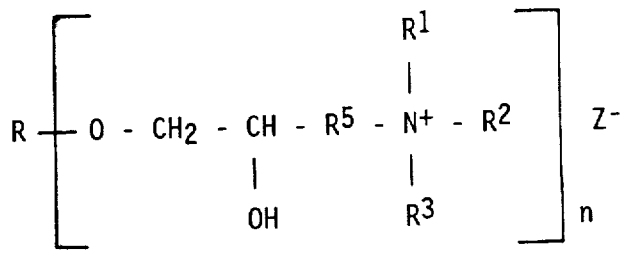

where R represents guar gum; $R^5$ is an alkylene group containing from one to three carbon atoms; $R^1$, $R^2$ and $R^3$ are radicals containing not more than 18 carbon atoms; Z is an anion; and n corresponds to a degree of substitution of from about 0.11 to about 0.22;

3. from 12% to 60% of a moisturizer selected from the group consisting of sodium pyrrolidone carboxylic acid, sodium lactate, hexadecyl, myristyl, isodecyl, or isopropyl esters of adipic, lactic, oleic, stearic, isostearic, myristic and linoleic acids, and their corresponding alcohol esters, sodium isostearoyl-2-lactylate and sodium capryl lactylate, glycerin, polyethylene glycol, propylene glycol, sorbitol, polyethylene

UNITED STATES PATENT AND TRADEMARK OFFICE
CERTIFICATE OF CORRECTION

PATENT NO. : 5,002,680

DATED : March 26, 1991

INVENTOR(S) : Robert R. Schmidt, Raymond H. Fortna & Harold H. Beyer

It is certified that error appears in the above-identified patent and that said Letters Patent is hereby corrected as shown below:

glycol and propylene glycol ethers of methyl glucose, polyethylene glycol and propylene glycol ethers of lanolin alcohol, lactic acid, L-proline, other free fatty acids, and mixtures thereof; and wherein when said moisturizer is selected from the group consisting of only said glycerine, said sorbitol, said polyethylene glycol and mixtures thereof, said level of moisturizer is present at at least 12% of said concentrate and wherein said glycerine is present at a level of at least about 12%;

UNITED STATES PATENT AND TRADEMARK OFFICE
CERTIFICATE OF CORRECTION

PATENT NO. : 5,002,680

DATED : March 26, 1991

INVENTOR(S) : Robert R. Schmidt, Raymond H. Fortna & Harold H. Beyer

It is certified that error appears in the above-identified patent and that said Letters Patent is hereby corrected as shown below:

4. balance water; and

B. from 3% to 12% of a propellant by weight of the total emulsion said cleansing product being formulated to provide a pH in use within the range of from about 5 to about 6. --

(The above Claim was entered originally as Claim 31 (Four times amended) in the Amendment dated Sept. 25, 1990.)

Signed and Sealed this

Thirtieth Day of March, 1993

Attest:

STEPHEN G. KUNIN

*Attesting Officer*      *Acting Commissioner of Patents and Trademarks*